[19] United States Patent
Frayman

[11] Patent Number: 5,531,674
[45] Date of Patent: Jul. 2, 1996

[54] COMPACTLY ASSEMBLED TAMPON APPLICATOR

[76] Inventor: Max Frayman, 25 Quinnehtuk Cir., Longmeadow, Mass. 01106

[21] Appl. No.: 369,713

[22] Filed: Jan. 6, 1995

[51] Int. Cl.⁶ ..................................... A61F 13/20
[52] U.S. Cl. .................. 604/11; 604/15; 604/904
[58] Field of Search ................... 604/1–3, 11–18, 604/904

[56] References Cited

U.S. PATENT DOCUMENTS 4,479,791  10/1984  Sprague ..................................... 604/16
4,726,805  2/1988   Sanders, III ............................... 604/15

FOREIGN PATENT DOCUMENTS 0355396  2/1990  European Pat. Off. ............... 604/904

Primary Examiner—Mary Beth Jones
Assistant Examiner—Dennis Ruhl

[57] ABSTRACT

A tampon applicator assembly of the compact type is provided comprising an outer tube, an inner tube slidably nested therein and a tampon stored inside of the inner tube. A small portion of the tampon is protruding from a proximal end of the inner tube. The inner tube has to be partially withdrawn from the outer tube in the distal direction to prepare the applicator for use. To prevent significant distal displacement of the tampon relative to the outer tube during the partial withdrawal, the outer tube comprises a holding means. The holding means comprises a set of circumferentially located pivotable clamp dogs at the location of the protruding portion of the tampon. Each clamp dog fixed to the inner surface of the outer tube by a spring hinge keeping a catching edge of the clamp dog constantly pressed against the tampon. If a longitudinal force is applied to the tampon in the distal direction the tampon jams itself. The tampon can be easily expelled through a proximal discharge end of the outer tube by the force applied to the tampon in the proximal direction.

4 Claims, 1 Drawing Sheet

COMPACTLY ASSEMBLED TAMPON APPLICATOR

BACKGROUND OF THE INVENTION

The present invention relates to a tampon insertion device and, more particularly, to a preferably short and compact type.

The tampon applicator assembly consists of an outer tube (the insertion tube or barrel)having a forward end (leading end or insertion end, or distal discharge end), a tampon positionable within the outer tube immediately inward of its leading end, and an inner tube (ejection tube or plunger, or pusher, or ejector) telescopically receivable within the outer tube rearwardly of the tampon and functioning as the pusher for effecting the forward delivery of the tampon through the leading end of the outer tube.

As known, the tampon applicator is vaginally introducible and, subsequent to the forward delivery of the tampon, is withdrawable.

Tampon applicators are commonly of two types, distinguished from each other by their length.

Conventional type applicators are usually of the ready-for-use type whereas compact type applicators have to be prepared for use by the user.

In the conventional type applicator, the tampon is located inside the leading portion of the outer rube, and the inner tube or the pusher is located within the outer tube rearwardly of the tampon.

In the compact type applicator, the tampon (or at least the greater portion thereof) is located within the inner tube. In operational use, the user has to hold the rear end of the outer tube by the fingers of one hand and grip the rear end of the inner tube to retract it by the fingers of the other hand so that the front end of the inner tube will be behind the rear end of the tampon.

To facilitate inner tube retraction, any compact applicator has to comprise a tampon holding means associated with the outer tube for engaging a tampon carried in the inner tube so as to resist rearward movement of the tampon, while permitting its forward movement through the discharge end of the outer tube during expulsion of the tampon into the body cavity.

Lately a lot of structural solutions of the tampon holding means, which can be divided into three major groups, have been introduced.

The first group includes the applicators which comprise an additional part, such as the inner sleeve located between the inner and outer tubes shown in U.S. Pat. No. 4,676,773. The necessity to fabricate an additional part and the using of more complicated assembling machinery disadvantageously increase the cost of production of such tampon applicators. Besides, the tampon applicator according to U.S. Pat. No. 4,676,773 suffers disadvantage from the user's safety standpoint. Very often the rear end of a tampon has an unbound particle, which, in this particular applicator structure, can be tangled between ring 12 and folded flange 11 (see FIG. 11 of U.S. Pat. No. 4,676,773). If this happened, the outer tube will be withdrawn alone. The withdrawal of the remaining parts of the applicator can necessitate emergency medical assistance.

The second group includes the applicators, in which the tampon holding means comprises at least one projection, fixed to the inner surface of the outer tube, extending inwardly through a longitudinal window in the inner tube and located rearwardly of the rear end of the tampon. Such applicators are described in U.S. Pat. Nos. 4,276,881; 4,286,595; 4,291,596; 4,891,042. All applicators of this group suffer from the same disadvantage following from necessity of additional rotational orientation of the tubes prior to the assemblage of the applicator.

The third group includes the applicators in which the tampon holding means are located adjacent of the discharge end of the outer tube and coacts with the front end of the tampon. The applicator described in U.S. Pat. No. 4,479,791 has a tampon completely stored in the inner space of the inner tube and tampon holding means in the form of thin elongated projections extending from the inner surface of the outer tube inwardly through the openings between the long fingers of the inner tube. Because of such structure, this applicator suffers the same disadvantage as the second group of applicators. Another disadvantage follows from a weakness of narrow long fingers of the inner tube. Sometimes they are not able to transfer to the tampon the longitudinal force applied to the rear end of the inner tube during expulsion of the tampon. If they are bent and smashed, the tampon will be positioned improperly. Besides, if the tampon is highly compressed, those projections can be bent in the circumferential direction during the assembly of the applicator. In this case, the projections loose ability to hold the tampon during partial withdrawal of the inner tube and such applicator cannot be used.

Each of the above listed patents is assigned to one of the major tampon manufacturers, but none of those tampon applicators had been commercially successful so far.

At the present time only one compact tampon applicator is commercially available, and it is fabricated in accordance with U.S. Pat. No. 4,726,805 (used hereby as a reference). This patent describes an applicator with a tampon holding means comprising a set of flaps located circumferentially closely adjacent to the bases of the petals defining the leading end of the outer tube. Each flap is a thin circumferentially extended projection flexible in the axial direction.

The flaps cannot sufficiently hold the portion of the tampon extending from the inner tube, if the tampon is fabricated of straight cylindrical configuration. To increase the tampon holding effect the extended portion is made in the form of a head, enlarged in diameter and positioned in front of the flaps.

Actually, many of these tampons have misalignment of the head and the remaining portion. Such tampons have the shoulder behind the head on one side and do not have it on the diametrally opposed side. Functional reliability of the applicator assembled with such tampon decreases, especially if a user uses the applicator in an environment existing in a public toilet.

So, this applicator necessitates the use of more complicated tampon making machinery, but does not provide reliable enough tampon applicator assembly.

SUMMARY OF THE INVENTION

Accordingly, it is an object of this invention to provide a compact tampon applicator assembly that eliminates the above described difficulties and disadvantages.

More particularly, it is an object of this invention to provide a compact tampon applicator assembly with a highly reliable tampon holding means and, accordingly, to increase credence to a compact type applicator as such.

Another object of this invention is to provide a compact tampon applicator assembly which prevents any disturbances of the sensitive tissue of the vagina during insertion and withdrawal of the applicator.

Another object of this invention is to provide a compact tampon applicator assembly comprising components which can be easily fabricated by existing high speed production machinery. It is a further object of this invention to provide a compact tampon applicator, comprising highly reliable tampon holding means, which can be easily assembled without rotational orientation of the tubes.

Lastly, it is an object of this invention to provide a compact tampon applicator which satisfies certain environmental requirements by decreasing the bulk of wrapping and packaging materials and eliminating unrecyclable spoilages and rejects.

The foregoing and other objects of the invention are realized by a tampon applicator assembly provided with a tampon holding means, which comprises a set of circumferentially located pivotable clamp dogs fixed by thin attachments to the inner surface of the outer tube adjacent of bases of petals defining a leading discharge end. This holding means prevents movement of the tampon in the rearward direction very efficiently and yet also allows easy passage of the tampon in the forward direction, when the latter has to be expelled. The holding means according to the present invention can function properly and efficiently with the tampon having a simple configuration and any compression accepted in the industry.

Other features and advantages of the present invention will become apparent from the following description of the invention which refers to the accompanying drawings.

DESCRIPTION OF THE PREFERRED EMBODIMENTS

The preferred embodiments of the tampon applicator assembly incorporating the principles of this invention are shown in FIGS. 1 to 4.

Figure 1:
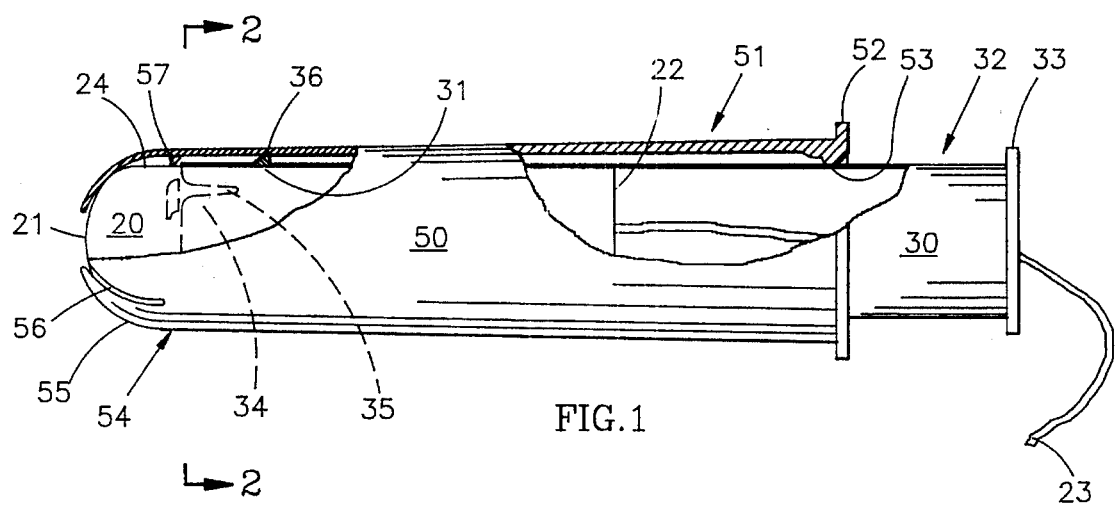
FIG. 1 is a partially sectioned longitudinal view of a tampon applicator according to present invention in the assembled position.

FIG. 1 illustrates the components of the assembly, namely a catamenial tampon 20, an inner tube 30, and an outer tube 50 in collapsed, prior-to-use position.

The assemblage and its components are shown with the proximal or front end on the readers left and the distal or rearward end on the readers right.

As shown in FIG. 1 the tampon 20 has a mostly cylindrical configuration with a slightly rounded proximal end 21 for easier insertion. From a rear edge 22 of tampon 20 extends a cord 23 for withdrawal of the used tampon 20 from the vagina. A small portion 24 of tampon 20 protrudes from a proximal end 31 of the inner tube 30 and the remaining portion 25 is stored therein.

The inner tube 30 is a generally cylindrical thin-walled tube comprising at a distal end 32, a flange 33 and at proximal end 31 is provided with a set of radially inwardly biased short fingers 34 divided by slots 35.

In fabrication, a diameter of an inscribed circle through free ends of fingers 34 is smaller than an outside diameter of tampon 20 and when inner tube 30 and tampon 20 are assembled together those diameters are equal.

On the outer surface of the inner tube 30 adjacent to fingers 34 there is a circumferential projection 36.

The outer tube 50 is a generally cylindrical thin-walled tube or slightly tapered to satisfy requirements of molding technology.

At a distal end 51 the outer tube 50 comprises a flange 52 on the outer surface and a circumferential projection 53 on the inner surface. The clear diameter of projection 53 is smaller than the maximum diameter of projection 36 on the inner tube 30.

Figure 2:
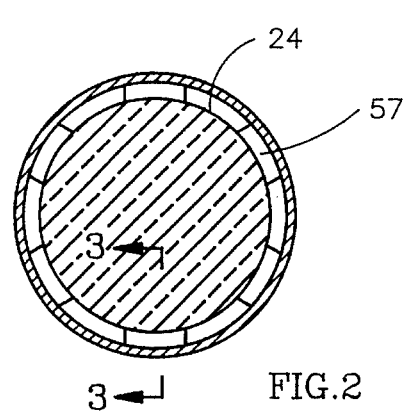
FIG. 2 is an enlarged sectional view taken on line 2—2 of the proximal end of the assembled applicator of FIG. 1.

A proximal discharge end 54 of outer tube 50 is closed by a set of radially inwardly based petals 55 divided by slots As shown in FIG. 1 and FIG. 2, on the inner surface of outer tube 50 adjacent to the bases of petals 55 there is a set of pivotable clamp dogs 57 circumferentially located and fixed thereto.

Figure 3:
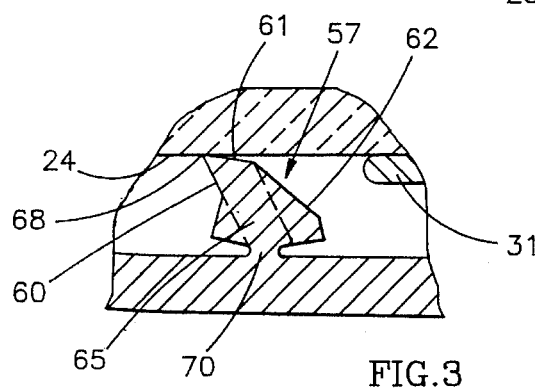
FIG. 3 is an enlarged sectional view taken on line 3—3 of a potion of the proximal end of FIG. 2, showing position of a clamp dog at assembly.
Figure 3A:
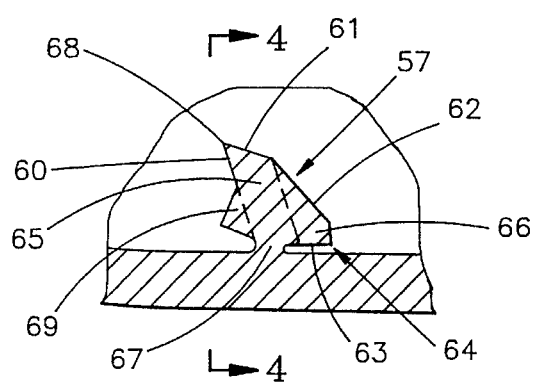
FIG. 3A is similar to FIG. 3 showing position of the clamp dog in fabrication.
Figure 4:
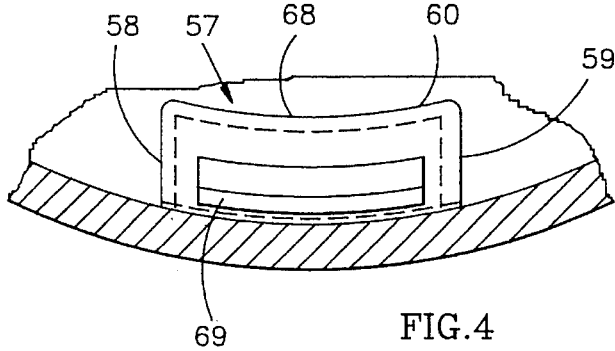
FIG. 4 is a sectional view taken on line 4—4 of the proximal end of the outer tube of FIG. 3A, showing another view of the clamp dog in fabrication.

As can be seen in FIG. 3A and FIG. 4, in fabrication each clamp dog 57 is enclosed by two longitudinal surfaces 58 and 59 and four circumferentially extending surfaces therebetween.

A proximally faced surface 60 is inclined to the axis of outer tube 50 approximately from 75° to 85°. An inwardly faced surface 61 is inclined to the tube axis approximately from 5° to 20°. A distally faced surface 62 is inclined to the tube axis approximately from 35° to 55°. An outwardly faced surface 63 is preferably parallel to the inner surface of outer tube 50 with a small clearance 64 therebetween. All above mentioned angles are measured from the axis to the surfaces in direction of a watch arm.

Clamp dog 57 fenced by surfaces 58, 59, 60, 61, 62, and 63 includes a tapered rigid arm 65 and a limiting arm 66, positioned distally of arm 65, One side of arm 65 fixed to the inner surface of outer tube 50 by a thin attachment 67 and the opposite side, which is free, has a catching edge 68 as result of crossing of surfaces 60 and 61.

If tampon 20 is fabricated with possible unbound particles at rear edge 22, it is advantageous to provide a projection 69 on surface 60, which does not allow the swing of clamp dog 57 in the proximal direction over the acceptable limit. Diameter of the inscribed circle through catching edges 68 is slightly smaller than diameter of tampon 20.

The assembly process consists of simple steps. First step includes placing of proximal end 21 of tampon 20 behind distal end 32 of inner tube 30 in the longitudinally aligned position, whereas tampon 20 can be pushed through the inner space of inner tube 30 until a small portion 24 will protrude therefrom.

The second step includes placing of an assembly of the tampon and the inner tube, made in the first step, so that the protruding small portion 24 of tampon 20 will be located behind flange 52 of outer tube 50 in longitudinally aligned position.

Next step includes movement of this couple into outer tube 50 until proximal end 21 of tampon 20 will reach inner surfaces of petals 55.

Before the end of this movement, tampon 20 coacts with surfaces 62 and 61 of clamp dogs 57 and swings all of them in the proximal direction around thin attachments 67.

As shown in FIG. 3, where tampon 20 has already swung clamp dogs 57, the thin attachments 67 are deformed and functioning as a spring hinges 70. A force created by spring hinge 70 keeps catching edge 68 constantly pressed against tampon 20. In this position, the set of clamp dogs 57 is ready to function as the tampon holding means.

Figure 3B:
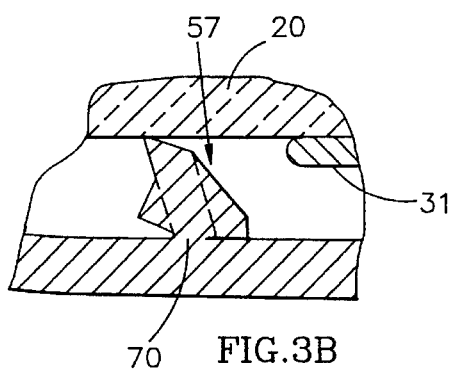
FIG. 3B is similar to FIG. 3 showing position of the clamp dog during retraction of the inner tube in the distal direction.

To prepare the applicator for use, a user has to withdraw inner tube 30 partially in the distal direction. By two fingers of one hand, the user has to hold distal end 51. By fingers of the other hand she has to grip distal end 32 and apply a distally directed longitudinal force. This force has be sufficient to slide inner tube 30 over tampon 20, i.e. to apply a force which is necessary to overcome friction between tampon 20 and inner tube 30. The same force in the same direction will be transferred to tampon 20. By action of this force tampon 20 is displaced on short distance in the distal direction as shown in FIG. 3B.

The distal displacement is approximately from 0.02 to 0.04 of an inch, but it is enough to swing clamp dog 57 in the distal direction so that clearance 64 disappeared. As soon as limiting arm 66 is pressed against the inner surface of outer tube 50, the tampon holding force increases very fast. Tampon 20 becomes jammed by the tampon holding means, and inner tube 30 continues the movement in the distal direction alone. This movement is ended when projection 36 is stretched against projection 53. In this position fingers 34 are positioned behind rear edge 22 of tampon 20. Now applicator is ready for use.

After the applicator is inserted into a body cavity, the user pushes inner tube 30 in the proximal direction and expels tampon 20 through proximal discharge end 54.

At the beginning of expelling, tampon 20 displaces catching edges 68 in the proximal direction. Clamp dogs 57 swing in the proximal direction too and take the positions, which they had at the assembly (see FIG. 3).

Although the present invention has been described in relation to a particular embodiment thereof, many other variations and modifications will become apparent to those skilled in the art.

Outer tube 50 and inner tube 30 may be constructed of materials, physical and chemical property of which are suitable for this kind of product and manufacturing process. Different amount of clamp dogs 57 in the set can be used depending on absorbency, hardness, and structure of tampon 20. Also clamp dog 57 may have different configurations. For example, limiting arm 66 and projection 69 can have a circumferential length as shown in FIG. 4 or extend to full length of rigid arm 65. Surface 62 may be concaved or convexed.

It is preferred, therefore, that the present invention be limited not by the specific disclosure herein, but by the scope of the appended claims.

I claim:

1. A compactly assembled tampon applicator and tampon comprising;

an elongated catamenial tampon shaped for vaginal insertion and having a predetermined diameter;

an inner tube having a proximal end for storing of said tampon so that a small portion of said tampon is protruding from said proximal end;

an outer tube dimensioned to fit telescopically over said inner tube and having a proximal discharge end, an inner surface, and an inner space defined by said inner surface; and a tampon holding means associated with said outer tube to prevent distal movement of said tampon during partial withdrawal of said inner tube over said tampon;

said holding means comprises at least one pivotable clamp dog, wherein said clamp dog is attached to said inner surface of said outer tube at a location where said tampon protrudes from said proximal end of said inner tube; said location defining an attachment point, said attachment point allowing said clamp dog to pivot with respect to a longitudinal axis of said outer tube;

said clamp dog extending radially from said inner surface of said outer tube towards a center of said outer tube, said clamp dog further comprising a first and second laterally extending projection such that when said clamp dog is pivoted in a first direction said first laterally extending projection will abut said inner surface of said outer tube to limit the distance said clamp dog can pivot in said first direction, and when said clamp dog is pivoted in a second direction, which is opposite the first direction, said second laterally extending projection will abut said inner surface of said outer tube to limit the distance said clamp dog can pivot in said second direction.

2. The compactly assembled tampon applicator and tampon of claim 1, wherein said clamp dog contacts said small portion of said tampon.

3. The compactly assembled tampon applicator and tampon of claim 1, wherein a portion of said clamp dog near said inner surface has a thickness that is less than a thickness of a portion of said clamp dog that is contacting said small portion of said tampon.

4. The compactly assembled tampon applicator and tampon of claim 3, wherein said inner and outer tubes are made of molded plastic having a stiffness of from 10,000–90,000 psi.

* * * * *